(12) United States Patent
Bone et al.

(10) Patent No.: US 11,027,057 B2
(45) Date of Patent: Jun. 8, 2021

(54) INTRAVENOUS (IV) TUBE ORGANIZATION AND LABELING APPARATUS AND SYSTEM

(71) Applicant: Crimson Medical Solutions, Pullman, WA (US)

(72) Inventors: Stephen J. Bone, Pullman, WA (US); Tyler L. D. Sager, Seattle, WA (US); Tanner J. Stahl, Salt Lake City, UT (US); Mitchell P. Weholt, Salt Lake City, UT (US)

(73) Assignee: Crimson Medical Solutions, Pullman, WA (US)

( * ) Notice: Subject to any disclaimer, the term of this patent is extended or adjusted under 35 U.S.C. 154(b) by 0 days.

(21) Appl. No.: 16/812,126

(22) Filed: Mar. 6, 2020

(65) Prior Publication Data

US 2021/0121622 A1 Apr. 29, 2021

Related U.S. Application Data

(60) Provisional application No. 62/927,597, filed on Oct. 29, 2019.

(51) Int. Cl.
| | |
|---|---|
| *A61M 5/00* | (2006.01) |
| *A61M 5/14* | (2006.01) |
| *A61M 39/08* | (2006.01) |
| *G09F 3/06* | (2006.01) |
| *F16B 7/04* | (2006.01) |
| *G09F 3/00* | (2006.01) |

(52) U.S. Cl.
CPC .......... *A61M 5/1418* (2013.01); *A61M 39/08* (2013.01); *F16B 7/0433* (2013.01); *G09F 3/0295* (2013.01); *G09F 3/06* (2013.01); *A61M 2205/583* (2013.01); *A61M 2205/6018* (2013.01); *A61M 2205/6081* (2013.01)

(58) Field of Classification Search
CPC ........ A61M 5/1418; A61M 2205/6018; A61M 2205/6081; A61M 2205/583; A61M 2205/584; A61M 39/08; A61M 2205/60; G09F 3/0295; G09F 3/06; F16B 7/0433
See application file for complete search history.

(56) References Cited

U.S. PATENT DOCUMENTS

| | | | | |
|---|---|---|---|---|
| 4,999,885 A | * | 3/1991 | Lee ..................... | A61M 5/1418 24/339 |
| 5,316,246 A | * | 5/1994 | Scott ................... | A61M 5/1418 248/68.1 |
| 5,876,371 A | * | 3/1999 | Yokoyama .......... | A61M 5/1413 128/DIG. 26 |
| 5,974,708 A | * | 11/1999 | Webb ..................... | A61M 5/14 40/316 |

(Continued)

*Primary Examiner* — Cassandra Davis
(74) *Attorney, Agent, or Firm* — Lee & Hayes, P.C.

(57) ABSTRACT

An intravenous (IV) tube organization apparatus includes at least one identification placard configured to couple to an IV tube. The identification placard includes a first tube capture portion configured to couple the identification placard to the IV tube, and a data portion to receive and display information regarding the IV tube. The IV tube organization apparatus also includes at least one arrangement clip configured to couple to the IV tube. The IV tube organization apparatus also includes a distinguishing characteristic to differentiate the apparatus from another apparatus.

18 Claims, 9 Drawing Sheets

(56) References Cited

U.S. PATENT DOCUMENTS

| | | | | |
|---|---|---|---|---|
| 7,455,662 | B2* | 11/2008 | Kraushaar | A61M 5/14 40/660 |
| 2007/0088286 | A1* | 4/2007 | Brier | A61M 5/1408 604/189 |
| 2012/0186116 | A1* | 7/2012 | Ohnishi | G09F 3/0295 40/316 |
| 2012/0260543 | A1* | 10/2012 | Dunn | G09F 3/06 40/316 |
| 2013/0053812 | A1* | 2/2013 | Lehmann | A61M 5/1418 604/403 |
| 2013/0138044 | A1* | 5/2013 | Schuman | G09F 3/205 604/174 |
| 2014/0082980 | A1* | 3/2014 | Sherman | G09F 3/205 40/316 |
| 2015/0272828 | A1* | 10/2015 | Pfanner | A61B 90/90 604/404 |
| 2017/0258984 | A1* | 9/2017 | Meyer | A61M 5/1418 |

* cited by examiner

INTRAVENOUS (IV) TUBE ORGANIZATION AND LABELING APPARATUS AND SYSTEM

RELATED APPLICATION

This application is a continuation of and claims priority to U.S. Provisional Patent Application Ser. No. 62/927,597, filed on Oct. 29, 2019, the entirety of which is incorporated by reference herein.

BACKGROUND

In the medical industry, liability for mistakes is a significant concern due to the huge costs that have been associated with such mistakes for many years. Among those mistakes that may be made, intravenous (IV) administration of fluids and/or pharmaceuticals present a particular liability. IV administration of a fluid and/or pharmaceutical includes direct injections or infusions of the fluid and/or pharmaceutical into the blood stream of a patient through a vein through the use of an IV administration device (also referred to herein as an "IV device"). Since delivery of the fluids and/or pharmaceuticals directly into a vein of the patient provides for one of the fastest ways to deliver the fluids and/or pharmaceuticals, very little or no time may be provided to remedy an incorrect dosage via the IV device. Accordingly, there is a need for constant improvement in the ability to mitigate harmful errors, especially with regard to errors surrounding IV administration of fluids and/or pharmaceuticals.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

DETAILED DESCRIPTION

Overview

This disclosure is directed to an apparatus for organizing and labeling IV tubing. In particular, the disclosure is directed to components of an apparatus useful for designating and maintaining IV tubing in an organized manner to mitigate medical errors related to inadvertent misuse of an IV tube. Such an error is most likely to occur when a patient is connected to more than one IV tube. As described above, because delivery of the fluids and/or pharmaceuticals directly into a vein of the patient provides for the fastest way to deliver the pharmaceuticals, very little or no time may be provided to remedy an incorrect dosage via the IV device. Accordingly, there is a need for constant improvement in the ability to mitigate harmful errors, especially with regard to errors surrounding IV administration of fluids and/or pharmaceuticals, and the present systems and methods mitigate medical errors by organizing IV tubing.

As used in the present specification and in the appended claims, the term "IV-deliverable composition" is meant to be understood broadly as any combination of fluids, crystalloids, colloids, blood, blood substitutes, albumin, plasma, saline, medications, pharmaceuticals, and/or other IV deliverable compositions. Further, the IV-deliverable composition includes any measure of a dosage of the IV-deliverable composition such as a volume or mass of the IV-deliverable composition.

Illustrative Embodiments of an IV Tube Management and Labeling Apparatus

Figure 1:
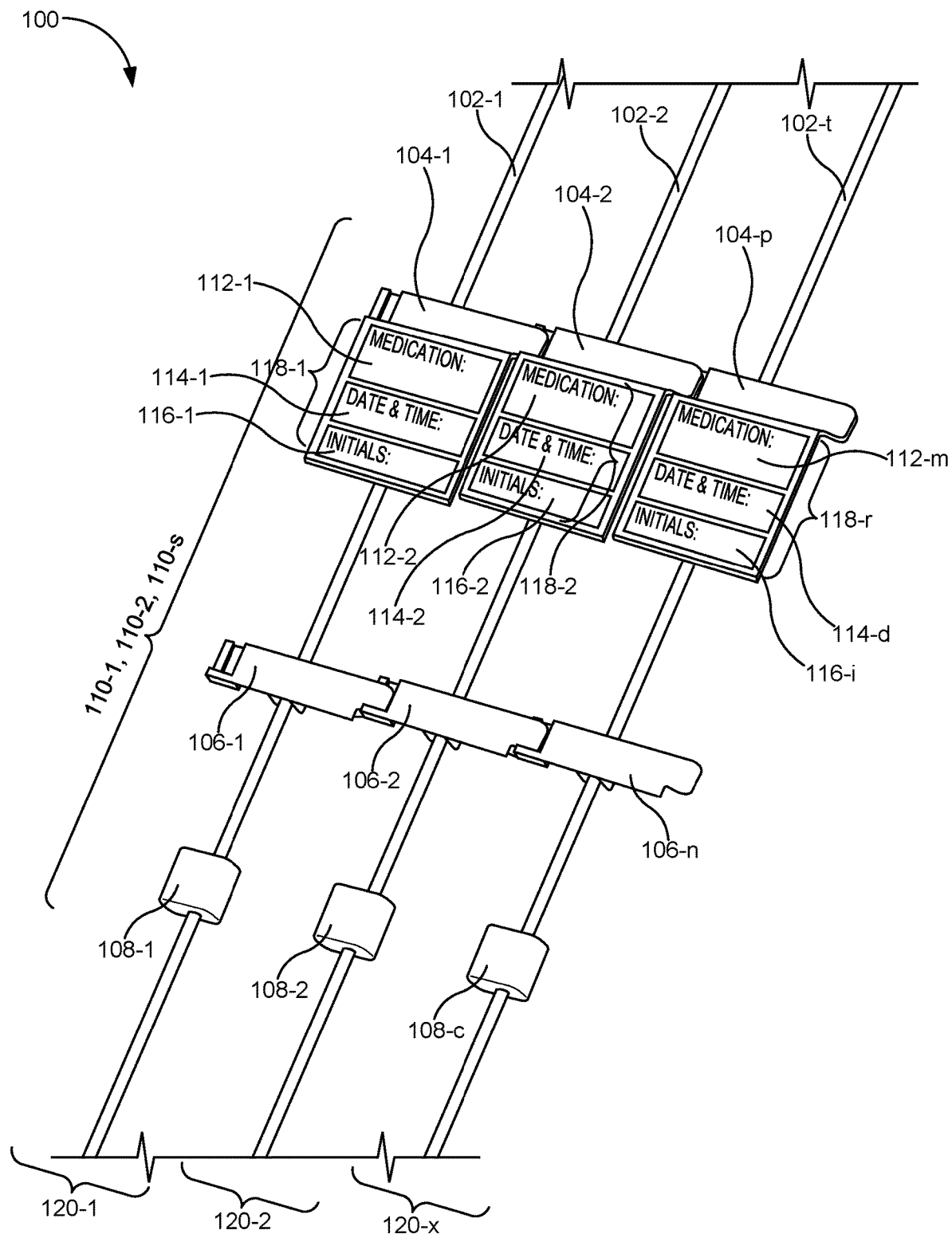
FIG. 1 is a perspective view of a plurality of IV tube organization and labeling apparatuses and system, according to an example of the principles described herein.

FIG. 1 is a perspective view of a system 100 of a plurality of IV administration sets 120-1, 120-2, . . . 120-x, where x is any integer greater than or equal to 1 (collectively referred to herein as "IV set(s) 120" unless specifically addressed otherwise). An IV set 120 includes at least one IV tube organization apparatus 110-1, 110-2, . . . 110-s, where s is any integer greater than or equal to 1 (collectively referred to herein as IV tube organization apparatus(es) 110 unless specifically addressed otherwise) and an IV tube 102-1, 102-2, . . . 102-t, where t is any integer greater than or equal to 1 (collectively referred to herein as IV tube(s) 102 unless specifically addressed otherwise). Nevertheless, an IV tube organization apparatus 110 may be provided separately from an IV tube 102. In FIG. 1, a set of three IV tube organization apparatuses 110 are depicted as applied to a corresponding number of IV tubes 102-1, 102-2, . . . 102-t.

The IV tubes 102 may include any recognized medical tube structure used for IV fluid delivery. Further, the IV tubes 102 may include a variety of associated devices coupled thereto. These associated devices may include, for example, a bag fluidically coupled to the IV tubes 102 to serve as a reservoir for the IV-deliverable composition, and an injection port within the bag through which an IV-deliverable composition may be injected. Further, the associated devices may include a drip chamber to measure a number of drops issued by the bag as measured in, for example, gutta per minute (gtt/min). Still further, the associated devices may include a number of injection ports located along a length of the IV tube 102 where an IV-deliverable composition may be injected directly into the IV tube 102. Even still further, the associated devices may include a roller clamp to adjust a rate of flow through the IV tubes 102 and/or slide clamps to stop or restrict the flow through the IV tubes 102.

In an embodiment, an IV tube organization apparatus 110 includes a first and largest component referred to herein as an identification placard 104-1, 104-2, . . . 104-$p$, where p is any integer greater than or equal to 1 (collectively referred to herein as identification placard(s) 104 unless specifically addressed otherwise). The identification placard 104 may include a data portion 118-1, 118-2, . . . 118-$r$, where r is any integer greater than or equal to 1 (collectively referred to herein as data portion(s) 118 unless specifically addressed otherwise). The data portion 118 may be located on the identification placards 104, and may include a space to provide information that may be written or otherwise presented (e.g., sticker, stamp, digitally scannable marker, visual note, etc.) to assist a medical professional, hospital staff, and pharmaceutical administrators, among others (collectively referred to herein as a medical practitioner) to identify what IV-deliverable composition may be or has been administered via the IV tube(s) 102 to which a respective identification placard 104 is coupled. The information included on the data portion 118 may include, for example, a medication entry 112-1, 112-2, . . . 112-$m$, where m is any integer greater than or equal to 1 (collectively referred to herein as medication entry(ies) 112 unless specifically addressed otherwise). The medication entry 112 may include a designation "Medication:" with an open area surrounding that designation where the IV-deliverable composition(s) that are or may be administered via the respective IV tube 102 is indicated. Indicating what IV-deliverable composition(s) are or may be administered via the respective IV tube 102 assists in mitigating harmful errors with regard to errors surrounding IV administration of IV-deliverable composition(s).

The information included on the data portions 118 of the identification placard 104 may also include, for example, a temporal entry 114-1, 114-2, . . . 114-$d$, where d is any integer greater than or equal to 1 (collectively referred to herein as temporal entry(ies) 114 unless specifically addressed otherwise). The temporal entry 114 may include a designation "Date & Time:" with an open area surrounding that designation where the date and time of the administration of the respective IV tube 102 and/or associated IV-deliverable composition(s) are administered via the respective IV tube 102 were or may be administered. Indicating when fluids and/or pharmaceuticals were administered or may be administered via the respective IV tube 102 also serves to mitigate harmful errors with regard to errors surrounding IV administration of pharmaceuticals by providing specific information as to when the respective IV tube 102 and/or associated fluids and/or pharmaceuticals were or are to be administered.

The information included on the data portion 118 of the identification placard 104 may also include, for example, an administrator identification entry 116-1, 116-2, . . . 116-$i$, where i is any integer greater than or equal to 1 (collectively referred to herein as administrator identification entry(ies) 116 unless specifically addressed otherwise). The administrator identification entry 116 may include a designation "Initials:" with an open area surrounding that designation where the administrator's initials, signature, or other designation that administered respective IV tube 102 and/or associated fluids and/or pharmaceuticals via the respective IV tube 102. Indicating who has or will administer the fluids and/or pharmaceuticals via the respective IV tube 102 also serves to mitigate harmful errors surrounding IV administration of pharmaceuticals by providing a source to which another individual may go to obtain more information about the respective IV tube 102 and/or associated fluids and/or pharmaceuticals administered.

In one example, the data portion 118 of the identification placard 104 including the medication entry 112, the temporal entry 114, and the administrator identification entry 116 may be presented as a preprinted label that includes the "Medication:", "Date & Time", and/or "Initials:", among other designations. In this example, the preprinted label may include a paper surface on which information may be written. In another example, the preprinted label may include a laminate surface on which non-permanent information may be recorded, erased, and used again to record other information.

In an embodiment not shown, the data portion 118 of the identification placard 104 may include an electronic display device such as a liquid-crystal display (LCD) writing tablet, a graphics tablet, a digitizer, an electronic drawing tablet, an electronic drawing pad, a digital drawing tablet, an electronic pen tablet, a digital art board, and a tablet computing device, among other writable and rewritable tablet devices.

The identification placards 104 may be coupled to one another via mating first and second ends as depicted in FIG. 1. For example, the first identification placard 104-1 includes a first fastener on a first end and a second fastener on a second end, the second identification placard 104-2 includes a first fastener on a first end and a second fastener on a second end, and the third identification placard 104-$p$ includes a first fastener on a first end and a second fastener on a second end. The first fastener and the second fastener for each identification placard 104 are formed to mate and couple with one another. Thus, the second fastener of the first identification placard 104-1 may mate and couple with the first fastener of the second identification placard 104-2, and the second fastener of the second identification placard 104-2 may mate and couple with the first fastener of the third identification placard 104-$p$ as arranged and depicted in FIG. 1. Any number of identification placards 104 may be coupled in this manner to arrange and identify the IV tubes 102. The first fastener and second fastener of the identification placards 104 are described further herein in connection with FIGS. 3A and 3B.

The IV tube organization apparatus 110 of the system 100 may also include a second component referred to herein as an arrangement clip 106-1, 106-2, . . . 106-$n$, where n is any integer greater than or equal to 1 (collectively referred to herein as arrangement clip(s) 106 unless specifically addressed otherwise). It is possible that the IV tubes 102 may become entangled one with another, and this entanglement may be the reason that errors surrounding IV administration of fluids and/or pharmaceuticals occur. Further, the IV tubes 102 may simply fall out of order further down the length of the IV tubes 102. The case of entanglement or disarrangement may still be the case even though the identification placards 104 may couple to one another and arrange the IV tubes 102. Thus, it may be beneficial to provide at least a second set of anchors, namely arrangement clips 106 along the length of the IV tubes 102 along with the identification placards 104 to mitigate entanglement and/or disarrangement of the IV tubes 102 that may lead to errors in IV administration of fluids and/or pharmaceuticals.

Like the identification placards 104, the arrangement clips 106 may be coupled to one another via a number of mating first and second ends as depicted in FIG. 1. The arrangement clips 106 may be coupled to one another via a number of mating first and second ends as depicted in FIG. 1. For example, the first arrangement clip 106-1 includes a first fastener on a first end and a second fastener on a second end, the second arrangement clip 106-2 includes a first fastener on a first end and a second fastener on a second end, and the third arrangement clip 106-n includes a first fastener on a first end and a second fastener on a second end. The first fastener and the second fastener for each arrangement clip 106 are formed to mate and couple with one another. Thus, the second fastener of the first arrangement clip 106-1 may mate and couple with the first fastener of the second arrangement clip 106-2, and the second fastener of the second arrangement clip 106-2 may mate and couple with the first fastener of the third arrangement clip 106-n as arranged and depicted in FIG. 1. Any number of arrangement clips 106 may be coupled in this manner to arrange the IV tubes 102. More regarding the first fastener and second fastener of the arrangement clips 106 are described herein in connection with FIGS. 4A and 4B.

The IV tube organization apparatus 110 of the system 100 may also include a third component referred to herein as a correlating clip 108-1, 108-2, . . . 108-c, where c is any integer greater than or equal to 1 (collectively referred to herein as correlating clip 108 unless specifically addressed otherwise). The correlating clip 108 may serve, like the identification placard 104 and the arrangement clip 106, to mitigate harmful errors surrounding IV administration of fluids and/or pharmaceuticals by providing another indicator that identifies the respective IV tube 102, with the identification placard 104 and/or the arrangement clip 106. The correlating clip 108 may be coupled to a respective one of the IV tubes 102 through a use of a tube capture portion configured to attach to the IV tube 102. In one example, the correlating clip 108 may include opposing sides of a deformable material. The material from which the correlating clip 108 are made may include any material that may undergo elastic deformation where the deformation is temporary and returns to its original shape after removal of an applied force such as when an IV tube 102 is forced through the narrow opening and into a channel where the IV tube 102 may reside. For example, the correlating clip 108 may be made of plastics, metals, and other elastically deformable materials. The correlating clip 108 is used to further identify which IV tube 102 the identification placard 104 and arrangement clip 106 are identifying by being able to be placed anywhere along the length of the IV tube 102. Further, any number of correlating clips 108 may be placed on an IV tube 102 to identify that IV tube along any portion of the length of the IV tube 102.

In the examples described herein, the correlating clip 108 may include an identifying feature that is associated with their respective identification placards 104 and arrangement clips 106. For example, a first correlating clip 108-1 may include an identifying feature that is also included on the first identification placard 104-1 and the first arrangement clip 106-1. Similarly, a second correlating clip 108-2 may include an identifying feature that is also included on the second identification placard 104-2 and the second arrangement clip 106-2. Further, a third correlating clip 108-c may include an identifying feature that is also included on the third identification placard 104-p and the third arrangement clip 106-n. The identifying feature common among the identification placard 104, the arrangement clip 106, and the correlating clip 108 of a particular IV tube organization apparatus 110 may include, for example, a common color, texture, pattern, image, other distinguishing characteristic, or combinations thereof that indicates to a user that the identification placard 104, the arrangement clip 106, and the correlating clip 108 are a set used to identify a common IV tube 102 to which they are all coupled. In this manner, an IV tube organization apparatus 110 may be quickly identified along any length of the IV tube 102 to which it is coupled resulting in a reduction in or mitigation of errors related to inadvertent misuse and/or misidentification of an IV tube 102.

Figure 2:
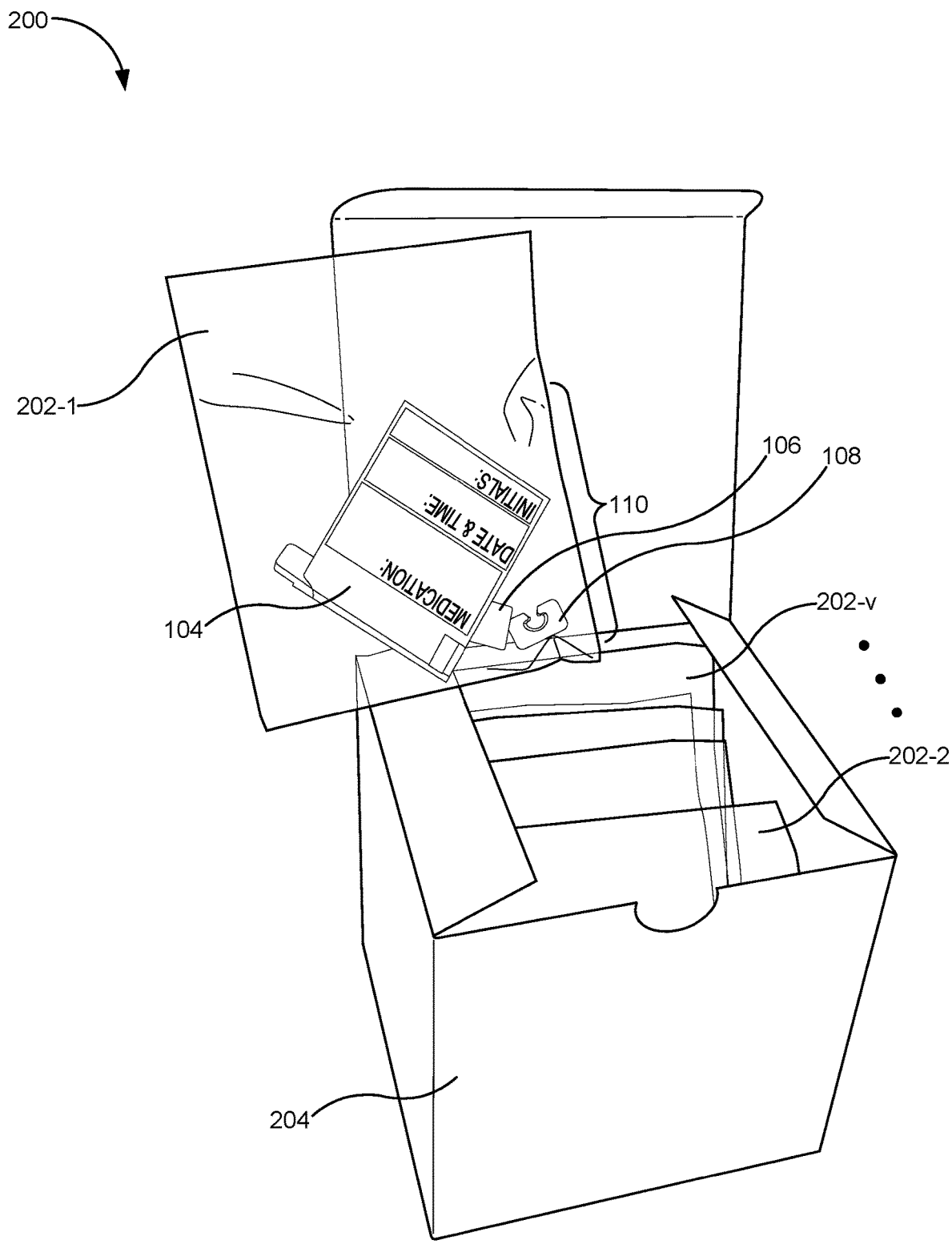
FIG. 2 is a perspective view of a plurality of IV tube organization and labeling apparatuses and system as packaged for distribution, according to an example of the principles described herein.

FIG. 2 is a perspective view of a package 200 containing a plurality of IV tube organization apparatuses 110 as packaged for distribution, according to an example of the principles described herein. Like many other types of medical supplies, the IV tube organization apparatuses 110 may be packaged to keep the IV tube organization apparatuses 110 individually separated until utilized in an IV administration scenario. A single IV tube organization apparatus 110 including at least one identification placard 104, at least one arrangement clip 106, and at least one correlating clip 108 may be packaged in individual package(s) 202-1, 202-2, . . . , 202-v, where v is any integer greater than or equal to 1 (collectively referred to herein as individual package(s) 202 unless specifically addressed otherwise). In the example of FIG. 2, the individual packages 202 may include a cellophane or similar transparent packaging that encapsulates the IV tube organization apparatus 110 so that the distinguishing characteristic of the IV tube organization apparatus 110 may be viewed by a user. For example, the IV tube organization apparatuses 110 in the individual packages 202 may include a distinguishing characteristic of color where a different IV tube organization apparatus 110 contained within different individual packages 202 are differently colored. Other distinguishing characteristics or combinations thereof may be used to distinguish the IV tube organization apparatuses 110 within their respective individual packages 202. In this manner, the user may select an IV tube organization apparatus 110 that is distinguishable over another IV tube organization apparatus 110 that may already be in use or is to be used together in administering IV-deliverable composition(s) to a patient.

In one example, the individual packages 202 may be opaque or at least partially opaque with a distinguishing characteristic that matches the distinguishing characteristic of the IV tube organization apparatus 110 included therein. For example, the individual packages 202 may have a color that matches a color of the IV tube organization apparatus 110 enclosed therein.

Package 200 may further include an assemblage packaging 204 to contain a plurality of the individual packages 202. In one example, a plurality of the individual packages 202 may be included within the assemblage packaging 204 where at least one of the plurality of individual packages 202 has a distinguishing characteristic that is different from at least another individual package 202. In this example, a plurality of IV tube organization apparatuses 110 with different distinguishing characteristics may be included within the assemblage packaging 204. This allows for the IV tube organization apparatuses 110 with different distinguishing characteristics to be used in connection with the administration of a plurality of IV-deliverable compositions to one or more patients and mitigate any errors that may result in confusing the different IV tubes 102. In practice, a first IV tube organization apparatus 110-1 with a first distinguishing characteristic may be coupled to a first IV tube 102-1. A second IV tube organization apparatus 110-2 with a second distinguishing characteristic different from the first distinguishing characteristic may be coupled to a second IV tube 102-2. A third IV tube organization apparatus 110-s with a third distinguishing characteristic different from the first and second distinguishing characteristics may be coupled to a third IV tube 102-t. The same may be arranged for any number of additional IV tube organization apparatuses 110 in order to distinguish different IV tubes 102 from one another.

With reference again to FIG. 2, the IV tube organization apparatus 110 may be sold as individual packages 202 and/or as a plurality of individual packages 202 included within the assemblage packaging 204. In this example, a user may obtain a plurality of IV tube organization apparatuses 110 to organize a corresponding number of IV tubes 102. In one example, the individual packages 202 may include medical-grade packaging materials, may be packaged using medial-based processes including sterilization processes, and/or may be designed based on medical-based standards and practices. In the examples described herein, the IV tube organization apparatuses 110 may be manufactured and packaged in a group as a system in the individual packages 202 for use as a system, and a plurality of the IV tube organization apparatuses 110 may be both packaged in the individual packages 202 and the assemblage packaging 204 to be used together as depicted in FIGS. 1 and 2.

Figure 3A:
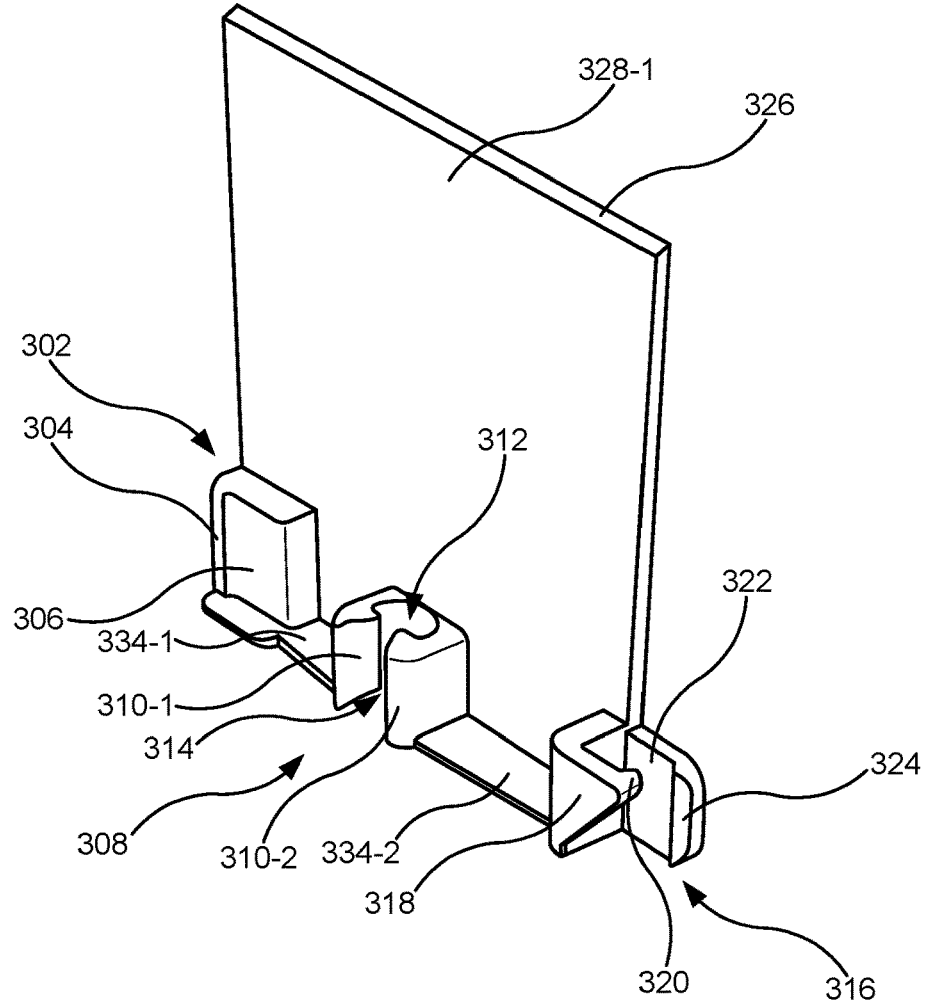
FIG. 3A is a rear-facing perspective view of an identification placard of the IV tube apparatus and system of FIG. 1, according to an example of the principles described herein.
Figure 3B:
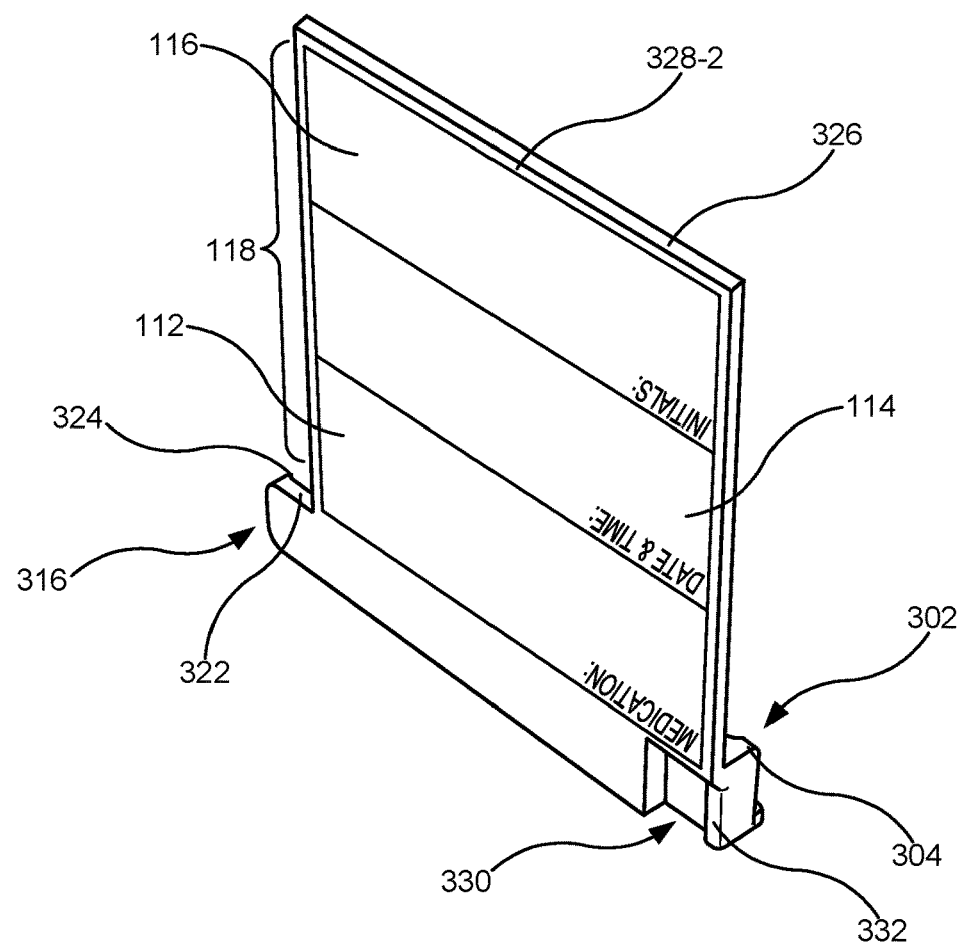
FIG. 3B is a front-facing perspective view of an identification placard of the IV tube apparatus and system of FIG. 1, according to an example of the principles described herein.

FIG. 3A is a rear-facing perspective view of an identification placard 104 of the IV tube organization apparatus 110 and system of FIG. 1, according to an example of the principles described herein. Further, FIG. 3B is a front-facing perspective view of the identification placard 104 of the IV tube organization apparatus 110 and system of FIG. 1, according to an example of the principles described herein. As described herein, a plurality of identification placards 104 may be coupled together as depicted in, for example, FIG. 1. Thus, an identification placard 104 includes a first anchor 302 formed on a first end, a first snap-fit fastener 316 formed on a second end, and a first tube capture portion 308 located between the first snap-fit fastener 316 and the first anchor 302. The first anchor 302, first tube capture portion 308, and the first snap-fit fastener 316 may be coupled to or formed on a first side 328-1 of the placard portion 326 of the identification placard 104. In one example, support structures 334-1, 334-2 may be formed between the first anchor 302 and the first tube capture portion 308, and the first tube capture portion 308 and the first snap-fit fastener 316, respectively to provide structural support and rigidity to the identification placard 104.

Although the first anchor 302 and the first snap-fit fastener 316 are depicted in FIGS. 3A and 3B, any type of mating fastening devices may be used to couple two identification placards 104 to one another. Other fasteners include, for example, clips, clasps, clamps, hook-and-eye closures, and snaps, among a myriad of other types of fasteners. In one example, the first end may include a magnetic element (embedded or exposed) with a first dipole, and the second end may also include a magnetic element (embedded or exposed) a second dipole opposite the first dipole such that when two identification placards 104 are brought in proximity to one another, the opposite first and second dipoles may attract and magnetically couple the identification placards 104.

In the example of FIGS. 1 through 3B, the first anchor 302 located on the first end may include a base portion 306 protruding from the placard portion 326 of the identification placard 104. A protrusion 304 may extrude from the base portion 306. Further, a recess 330 may be defined within a second side 328-2 of the placard portion 326. The recess 330 may be formed in the second side 328-2 of the placard portion 326 offset from the edge of the first end such that a ridge 332 is formed between the recess 330 and the edge of the placard portion 326. Mating elements of the first snap-fit fastener 316 may engage with the elements of the first anchor 302.

Thus, on the second end of the identification placard 104, the first snap-fit fastener 316 is formed and may include a first arm 318 protruding from the placard portion 326. The first snap-fit fastener 316 may include a cantilever snap-fit fastener where a deformable and/or deflectable lever or pin is moved in order to effectuate or undo the snap-fit. The first arm 318 includes a bend along its length such that the first arm 318 initially extends perpendicular to a first side 328-1 of the placard portion 326, and extends away from the placard portion 326 in parallel with a length of the placard portion 326. The first arm 318 may include a first catch 320 formed on the end of the first arm 318. As a first identification placard 104-1 is moved into a coupling position with, for example, the second identification placard 104-2, the first snap-fit fastener 316 of the first identification placard 104-1 may engage with the first anchor 302 of the second identification placard 104-2 by the deflection of the first arm 318 and first catch 320 of the first snap-fit fastener 316 around the protrusion 304 of the first anchor 302. As the first catch 320 passes the protrusion 304, the first arm 318 and first catch 320 return to an original, non-deflected position. In this state, the protrusion 304 assists in retaining engagement between the first anchor 302 and the first snap-fit fastener 316 since a force sufficient to at least deflect the first arm 318 and first catch 320 is required to separate the first identification placard 104-1 from the second identification placard 104-2.

The first snap-fit fastener 316 further includes a second arm 322 extending away from the placard portion 326 in parallel with a length of the placard portion 326. The second arm 318 includes a second catch 324 formed on a distal end of the second arm 322. As the first identification placard 104-1 is moved into a coupling position with, for example, the second identification placard 104-2, the first snap-fit fastener 316 of the first identification placard 104-1 may engage with the first anchor 302 of the second identification placard 104-2 by the deflection of the second arm 322 and the second catch 324 of the first snap-fit fastener 316 around a ridge 332. The second catch 324 passes the ridge 332, the second arm 322 and the second catch 324 return to an original, non-deflected position. In this state, the ridge 332 assists in retaining engagement between the first anchor 302 and the first snap-fit fastener 316 since a force sufficient to at least deflect the second arm 322 and second catch 322 is required to separate the first identification placard 104-1 from the second identification placard 104-2. In this manner, the first identification placard 104-1 and the second identification placard 104-2 may be coupled together. Further, any number of identification placards 104 may be coupled together in this manner as depicted in FIG. 1, where the first identification placard 104-1, the second identification placard 104-2, and the third identification placard 104-p are depicted as being coupled together in the manner described herein.

The identification placards 104 may also include the first tube capture portion 308. The first tube capture portion 308 may be any type of device that couples the identification placards 104 to their respective IV tubes 102. In the examples described herein, the first tube capture portion 308 may be referred to as a c-clip given its c-shaped cross-section. In the examples described herein, the identification placards 104 may include a pair of opposing jaws 310-1, 310-2 extending from the first tube capture portion 308. The jaws 310-1, 310-2 are separated by an opening 314 defined in the first tube capture portion 308. A channel 312 may also be defined within the first tube capture portion 308. A width of the opening 314 is narrower than the width of the channel 312 such that when an IV tube 102 is forced between the jaws 310-1, 310-2 and into the channel 312, the portion of the jaws 310-1, 310-2 that abut the channel 312 retain the IV tube 102 in the channel 312. In practice, the IV tube 102 and/or the jaws 310-1, 310-2 may be subjected to elastic deformation when the identification placard 104 is coupled to the IV tube 102. The IV tube 102 and/or the jaws 310-1, 310-2 deflect and/or deform from an original shape when the IV tube 102 is inserted between the jaws 310-1, 310-2 of the identification placard 104, and the IV tube 102 and/or the jaws 310-1, 310-2 return to the original, undeflected and/or undeformed shape when the IV tube 102 is seated within the channel 312. Coupling the identification placards 104 in this manner assists in organizing the respective IV tubes coupled to the identification placards 104 by arranging the IV tubes 102 in a visually perceptible manner. With this organization, a medical practitioner may be able to easily identify which of the several IV tubes 102 fluidically deliver which IV-deliverable composition.

In the examples described herein, the first anchor 302, the first tube capture portion 308, and/or the first snap-fit fastener 316 may be monolithically formed with the placard portion 326. In another example, the first anchor 302, the first tube capture portion 308, and/or the first snap-fit fastener 316 may be coupled to the placard portion 326 through, for example, plastic welding processes, gluing, and other coupling processes.

The second side 328-2 of the placard portion 326 of the identification placard 104 may include the medication entry 112, the temporal entry 114, the administrator identification entry 116 of the data portions 118 as depicted in FIGS. 1-3B. Although not depicted, in one example, the first side 328-1 of the placard portion 326 of the identification placard 104 may also include data portions as well as the second side 328-2 to provide more surface area on which additional information may be recorded.

Figure 4A:
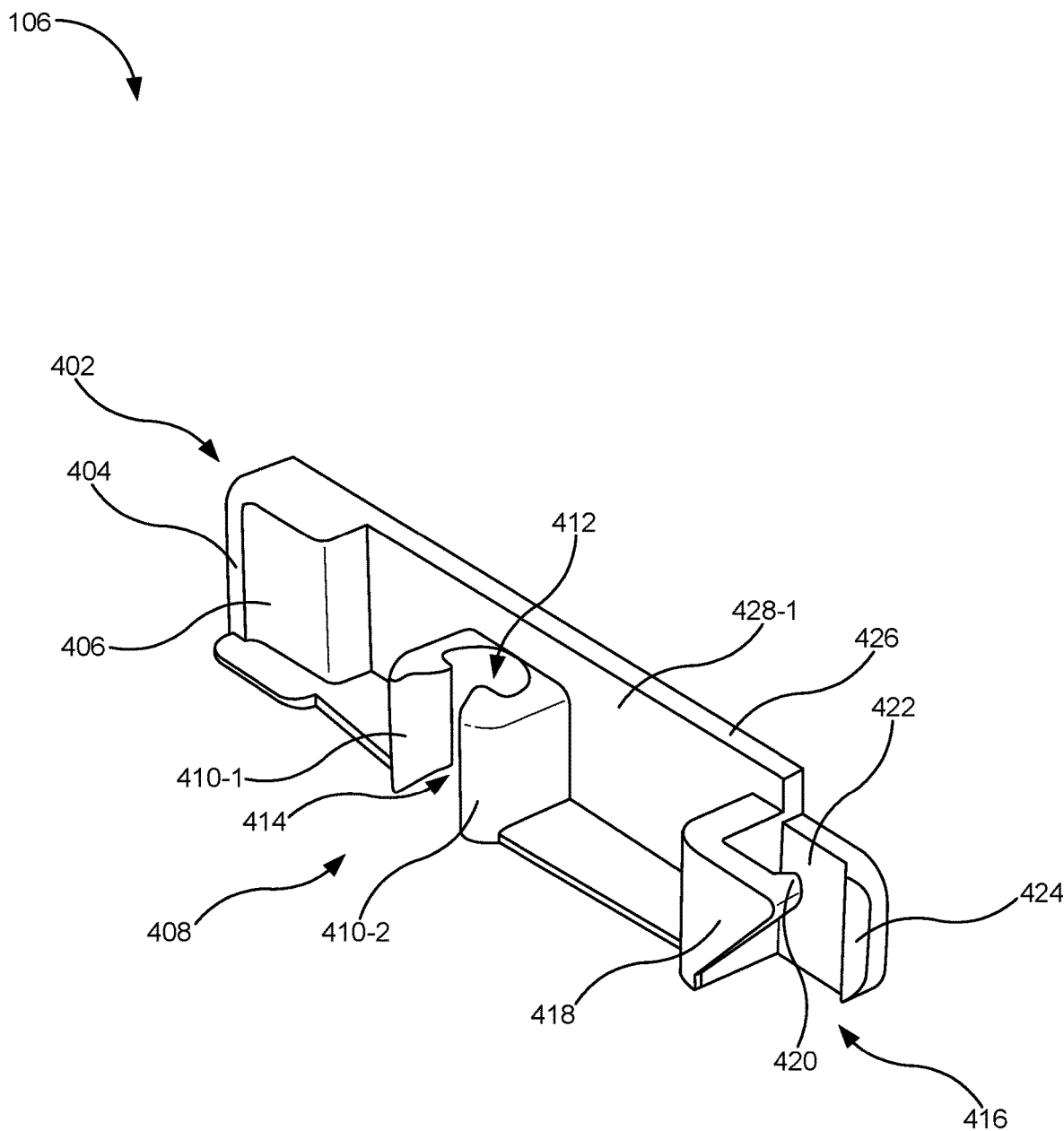
FIG. 4A is a rear-facing perspective view of an arrangement clip of the IV tube apparatus and system of FIG. 1, according to an example of the principles described herein.
Figure 4B:
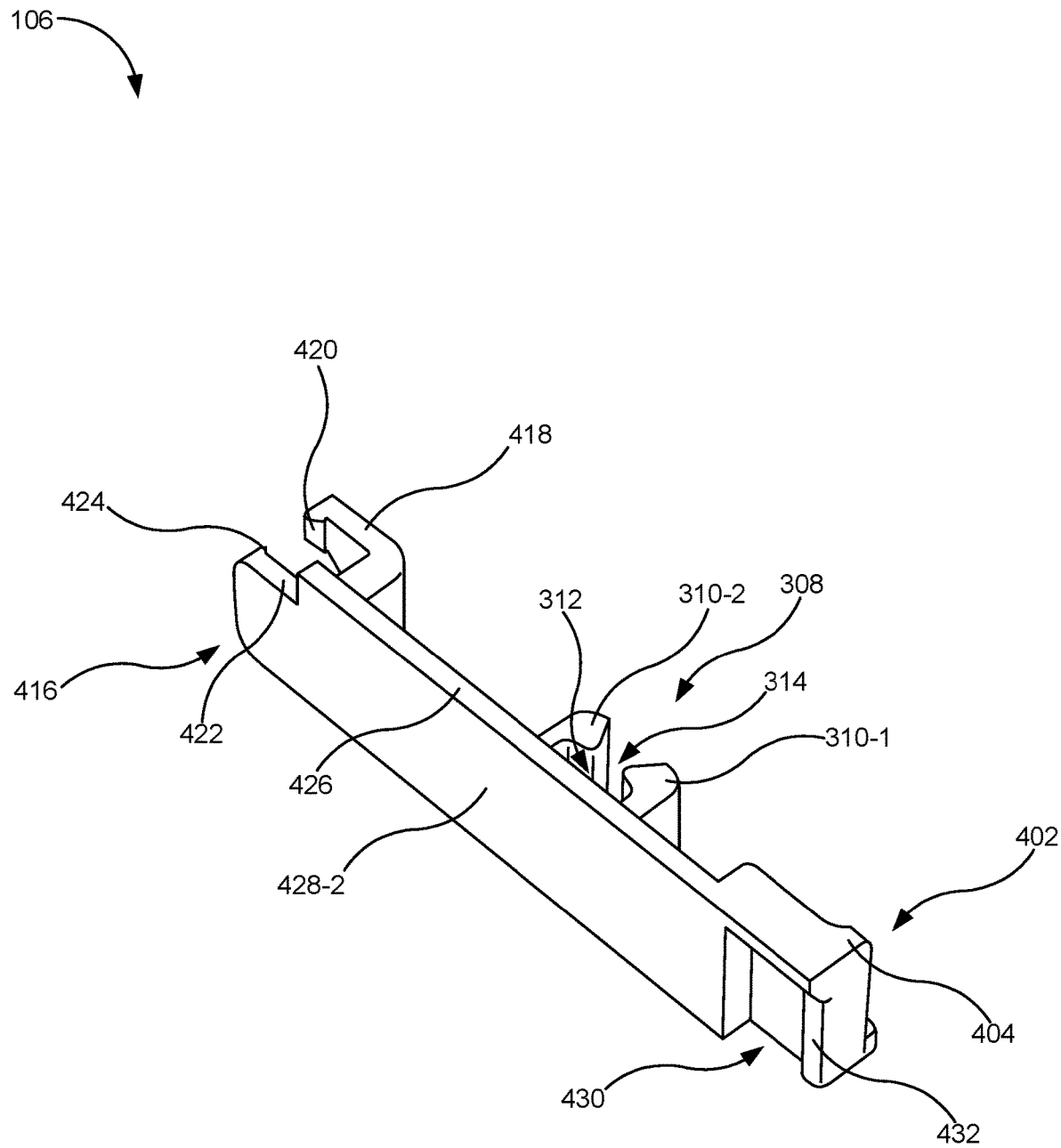
FIG. 4B is a front-facing perspective view of an arrangement clip of the IV tube apparatus and system of FIG. 1, according to an example of the principles described herein.

FIG. 4A is a rear-facing perspective view of an arrangement clip 106 of the IV tube apparatus and system 100 of FIG. 1, according to an example of the principles described herein. FIG. 4B is a front-facing perspective view of the arrangement clip 106 of the IV tube apparatus and system 100 of FIG. 1, according to an example of the principles described herein. As described herein, a plurality of arrangement clip 106 may be coupled together as depicted in, for example, FIG. 1 and as similarly described herein in connection with the identification placards 104. The coupling of a plurality of arrangement clips 106 together assists in organizing IV tubes 102 coupled to the respective arrangement clips 106. Further, when used in connection with the identification placards 104 as depicted in FIG. 1, the identification placards 104 and arrangement clips 106 provide organization of the IV tubes 102 along the length of the IV tubes 102 such that two anchor points for every IV tube 102 of the plurality of IV tubes 102 are created. Further, as the IV tubes 102 hang from a stand, the IV tubes 102 may become tangled or misarranged along the length of the IV tubes 102. The use of both the identification placards 104 and arrangement clips 106 ensure that the IV tubes 101 remain in an organized state further along the length of the IV tubes 102. The arrangement clips 106 described herein include elements similar to those elements of the identification placards 104. In another example, the elements of the arrangement clips 106 including those used to couple the arrangement clips 106 together may be the same or different from the elements of the identification placards 104.

An arrangement clip 106 includes a second anchor 402 formed on a first end, a second snap-fit fastener 416 formed on a second end, and a second tube capture portion 408 located between the second snap-fit fastener 416 and the second anchor 402. The second anchor 402, second tube capture portion 408, and the second snap-fit fastener 416 may be coupled to or formed on a first side 428-1 of a backing portion 426 of the arrangement clip 106. In one example, support structures 434-1, 434-2 may be formed between the second anchor 402 and the second tube capture portion 408, and the second tube capture portion 408 and the second snap-fit fastener 416, respectively, to provide structural support and rigidity to the arrangement clip 106.

Although the second anchor 402 and the second snap-fit fastener 416 are depicted in FIGS. 4A and 4B, any type of mating fastening devices may be used to couple two arrangement clips 106 to one another. Other fasteners include, for example, clips, clasps, clamps, hook-and-eye closures, and snaps, among a myriad of other types of fasteners. In one example, the first end may include a magnetic element with a first dipole, and the second end may also include a magnetic element a second dipole opposite the first dipole such that when two arrangement clips 106 are brought in proximity to one another, the opposite first and second dipoles may attract and magnetically couple the arrangement clips 106.

In the example of FIGS. 1, 2, 4A, and 4B, the second anchor 402 located on the first end may include a base portion 406 protruding from the backing portion 426 of the arrangement clip 106. A protrusion 404 may extend from the base portion 406. Further, a recess 430 may be defined within a second side 428-2 of the backing portion 426. The recess 430 may be formed in the second side 428-2 of the backing portion 426 offset from the edge of the first end such that a ridge 432 is formed between the recess 430 and the edge of the backing portion 426. Mating elements of the second snap-fit fastener 416 may engage with the elements of the second anchor 402.

Thus, on the second end of the arrangement clip 106, the second snap-fit fastener 416 is formed and may include a first arm 418 protruding from the backing portion 426. The second snap-fit fastener 416 may include a cantilever snap-fit fastener where a deformable and/or deflectable lever or pin is moved in order to effectuate or undo the snap-fit. The first arm 418 includes a bend along its length such that the first arm 418 initially extends perpendicular to a first side 428-1 of the backing portion 426, and extends away from the backing portion 426 in parallel with a length of the backing portion 426. The first arm 418 may include a first catch 420 formed on the end of the first arm 418. As a first arrangement clip 106-1 is moved into a coupling position with, for example, the second arrangement clip 106-2, the second snap-fit fastener 416 of the first arrangement clip 106-1 may engage with the second anchor 402 of the second arrangement clip 106-2 by the deflection of the first arm 418 and first catch 420 of the second snap-fit fastener 416 around the protrusion 404 of the second anchor 402. As the first catch 420 passes the protrusion 404, the first arm 418 and first catch 420 return to an original, non-deflected position. In this state, the protrusion 404 assists in retaining engagement between the second anchor 402 and the second snap-fit fastener 416 since a force sufficient to at least deflect the first arm 418 and first catch 420 is required to separate the first arrangement clip 106-1 from the second arrangement clip 106-2.

The second snap-fit fastener 416 further includes a second arm 422 extending away from the backing portion 426 in parallel with a length of the backing portion 426. The second arm 418 includes a second catch 424 formed on a distal end of the second arm 422. As the first arrangement clip 106-1 is moved into a coupling position with, for example, the second arrangement clip 106-2, the second snap-fit fastener 416 of the first arrangement clip 106-1 may engage with the second anchor 402 of the second arrangement clip 106-2 by the deflection of the second arm 422 and the second catch 424 of the second snap-fit fastener 416 around a ridge 432. The second catch 424 passes the ridge 432, the second arm 422 and the second catch 424 return to an original, non-deflected position. In this state, the ridge 432 assists in retaining engagement between the second anchor 402 and the second snap-fit fastener 416 since a force sufficient to at least deflect the second arm 422 and second catch 422 is required to separate the first arrangement clip 106-1 from the second arrangement clip 106-2. In this manner, the first arrangement clip 106-1 and the second arrangement clip 106-2 may be coupled together. Further, any number of arrangement clips 106 may be coupled together in this manner as depicted in FIG. 1, where the first arrangement clip 106-1, the second arrangement clip 106-2, and the third arrangement clip 106-$p$ are depicted as being coupled together in the manner described herein.

The arrangement clips 106 may also include the second tube capture portion 408. In the examples described herein, the second tube capture portion 408 may be referred to as a c-clip given its c-shaped cross-section. The second tube capture portion 408 may be any type of device that couples the arrangement clips 106 to their respective IV tubes 102. In the examples described herein, the arrangement clips 106 may include a pair of opposing jaws 410-1, 410-2 extending from the second tube capture portion 408. The jaws 410-1, 410-2 are separated by an opening 414 defined in the second tube capture portion 408. A channel 412 may also be defined within the second tube capture portion 408. A width of the opening 414 is narrower than the width of the channel 412 such that when an IV tube 102 is forced between the jaws 410-1, 410-2 and into the channel 412, the portion of the jaws 410-1, 410-2 that abut the channel 412 retain the IV tube 102 in the channel 412. In practice, the IV tube 102 and/or the jaws 410-1, 410-2 may be subjected to elastic deformation when the arrangement clip 106 is coupled to the IV tube 102. The IV tube 102 and/or the jaws 410-1, 410-2 deflect and/or deform from an original shape when the IV tube 102 is inserted between the jaws 410-1, 410-2 of the arrangement clip 106, and the IV tube 102 and/or the jaws 410-1, 410-2 return to the original, undeflected and/or undeformed shape when the IV tube 102 is seated within the channel 412. Coupling the arrangement clips 106 in this manner assists in organizing the respective IV tubes coupled to the arrangement clips 106 by arranging the IV tubes 102 in a visually perceptible manner. With this organization, a medical practitioner may be able to easily identify which of the several IV tubes 102 fluidically deliver which IV-deliverable composition.

In the examples described herein, the second anchor 402, the second tube capture portion 408, and/or the second snap-fit fastener 416 may be monolithically formed with the backing portion 426. In another example, the second anchor 402, the second tube capture portion 408, and/or the second snap-fit fastener 416 may be coupled to the backing portion 426 through, for example, plastic welding processes, gluing, and other coupling processes.

Figure 5A:
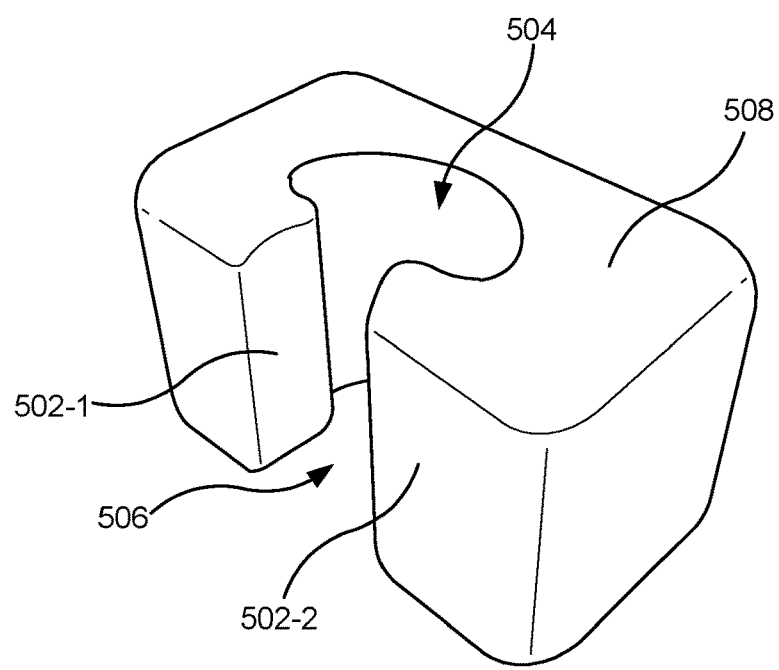
FIG. 5A is a rear-facing perspective view of a correlating clip of the IV tube apparatus and system of FIG. 1, according to an example of the principles described herein.
Figure 5B:
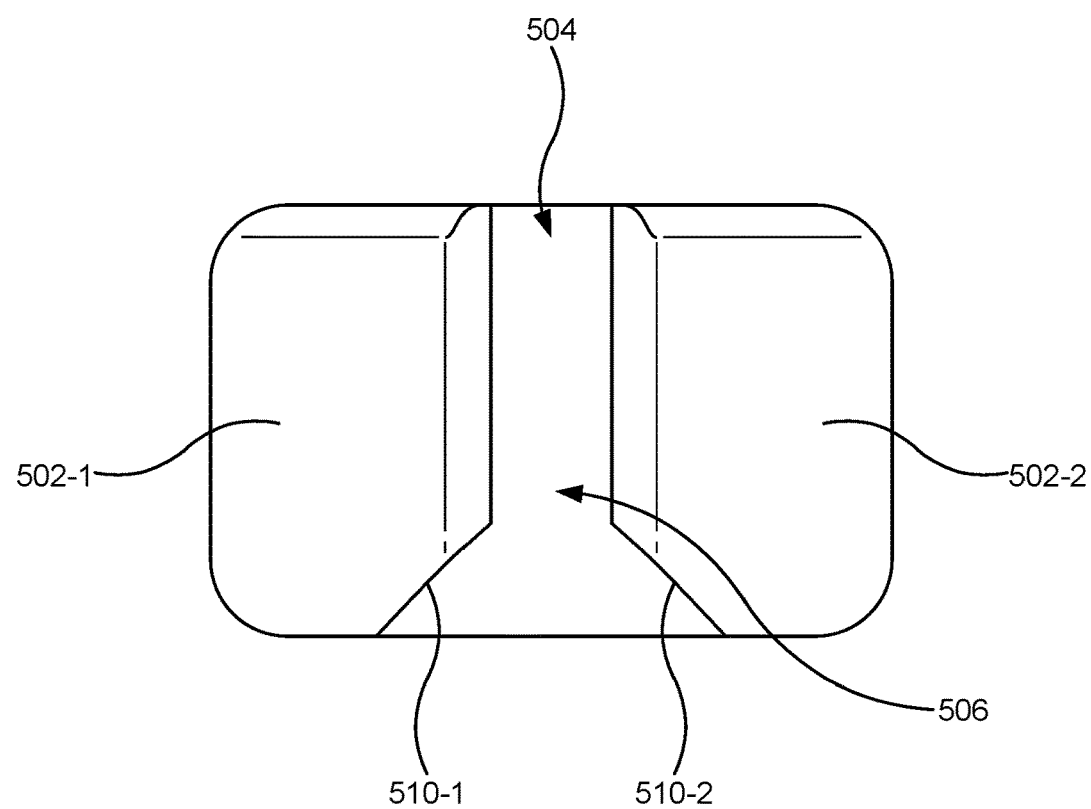
FIG. 5B is a rear, plan view of a correlating clip of the IV tube apparatus and system of FIG. 1, according to an example of the principles described herein.
Figure 5C:
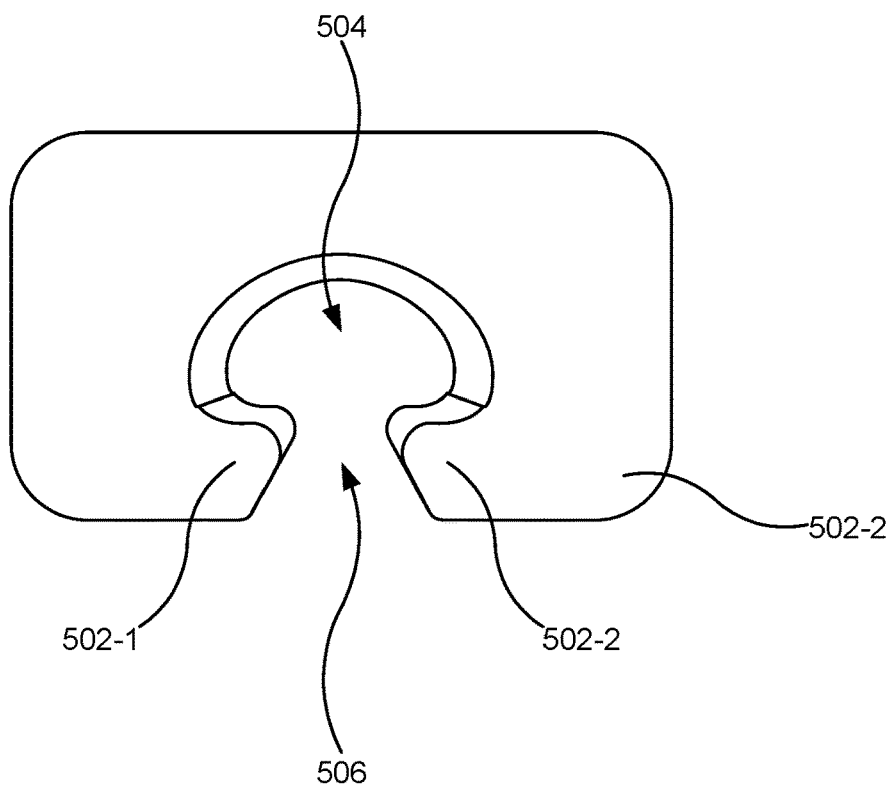
FIG. 5C is a top, plan view of a correlating clip of the IV tube apparatus and system of FIG. 1, according to an example of the principles described herein.

FIG. 5A is a rear-facing perspective view of a correlating clip 108 of the IV tube apparatus and system 100 of FIG. 1, according to an example of the principles described herein. Further, FIG. 5B is a rear, plan view of the correlating clip 108 of the IV tube apparatus and system 100 of FIG. 1, according to an example of the principles described herein. Still further, FIG. 5C is a top, plan view of the correlating clip 108 of the IV tube apparatus and system 100 of FIG. 1, according to an example of the principles described herein. As described herein, the correlating clips 108 may include an identifying feature that is associated with their respective identification placards 104 and arrangement clips 106. The identifying feature common among the identification placard 104, the arrangement clip 106, and the correlating clip 108 of a particular IV tube organization apparatus 110 may include, for example, a common color, texture, pattern, image, other distinguishing characteristic, or combinations thereof that indicates to a user that the identification placard 104, the arrangement clip 106, and the correlating clip 108 are a set used to identify a common IV tube 102 to which they are all coupled. In this manner, an IV tube organization apparatus 110 may be quickly identified along any length of the IV tube 102 to which it is coupled resulting in a reduction in or mitigation of errors related to inadvertent misuse and/or misidentification of an IV tube 102. By way of an example, the first IV tube organization apparatuses 110-1 including the first identification placard 104-1, the first arrangement clip 106-1, and the first correlating clip 108-1 may all include the same distinguishing characteristic. This allows a medical practitioner to consistently identify the associated first IV tube 102-1 along an entire length of the first IV tube 102-1.

In one example, a plurality of correlating clips 108 may be coupled to an IV tube 102 with each correlating clip 108 coupled to the same IV tube having the same distinguishing characteristic. In this example, the correlating clips 108 coupled to the same IV tube 102 may serve to assist a medical practitioner to identify which of a plurality of IV tubes 102 they are interacting with. For example, a correlating clip 108 may be coupled to the IV tube relatively closer to a bag fluidically coupled to the IV tube 102 to allow the medical practitioner to identify when interacting with the bag and while, for example, introducing an IV-deliverable composition into the bag. The medical practitioner may correlate the distinguishing characteristic of the correlating clip 108 with the distinguishing characteristics of the identification placards 104 and the arrangement clips 106 coupled to the IV tubes 102 within the system 100 to identify which of the identification placards 104 and the arrangement clips 106 correlate with that particular correlating clip 108. In this manner, the medical practitioner may be able to use the correlating clip 108 to identify which of a number of IV tubes 102 are to be used to deliver the IV-deliverable composition based on, for example, the information included on the correlating identification placard 104.

The correlating clip 108 may include similar elements with respect to the first tube capture portion 308 of the identification placards 104 and the second tube capture portion 408 of the arrangement clips 106. The correlating clips 108 may be any type of device that couples to a respective IV tube 102. In the examples described herein, the correlating clip 108 may be referred to as a c-clip given its c-shaped cross-section. In the examples described herein, the correlating clips 108 may include a pair of opposing jaws 502-1, 502-2 extending from a body portion 508. The jaws 502-1, 502-2 are separated by an opening 506 defined in the correlating clip 108. A channel 504 may also be defined within the correlating clip 108. A width of the opening 506 is narrower than the width of the channel 504 such that when an IV tube 102 is forced between the jaws 502-1, 502-2 and into the channel 504, the portion of the jaws 502-1, 502-2 that abut the channel 504 retain the IV tube 102 in the channel 504.

The correlating clips 108 may include a first angled portion 510-1 located on the first jaw 502-1 and a second angled portion 510-2 located on the second jaw 502-2. The angled portions 510-1, 510-2 may assist the medical practitioner in inserting the IV tube 102 into the correlating clip 108 by reducing an amount of friction between the IV tube and the correlating clip 108.

In practice, the IV tube 102 and/or the jaws 502-1, 502-2 may be subjected to elastic deformation when the correlating clip 108 is coupled to the IV tube 102. The IV tube 102 and/or the jaws 502-1, 502-2 deflect and/or deform from an original shape when the IV tube 102 is inserted between the jaws 502-1, 502-2 of the arrangement clip 106, and the IV tube 102 and/or the jaws 502-1, 502-2 return to the original, undeflected and/or undeformed shape when the IV tube 102 is seated within the channel 504.

Coupling the correlating clips 108 in this manner assists in organizing the respective IV tubes coupled to the correlating clip 108 by arranging the IV tubes 102 in a visually perceptible manner and correlating the identification placards 104 and arrangement clips 106 with the correlating clip 108. With this organization, a medical practitioner may be able to easily identify which of the several IV tubes 102 fluidically deliver which IV-deliverable composition.

In one example, the system 100 may include at least two components of the IV tube organization apparatuses 110 including the identification placard 104, the arrangement clip 106, and correlating clip 108. For example, the system 100 may include an identification placard 104 for each of the respective IV tubes 102, and at least one of the arrangement clip 106, and the correlating clip 108. Thus, the system 100 may include a first component including the identification placard 104, and a "second" component, which may refer to either of the aforementioned arrangement clip 106 or the correlating clip 108, each of which includes a tube capture portion.

When a medical practitioner seeks to utilize the system 100 for its IV tube 102 organizational and correlating properties, the identification placard 104, the arrangement clip 106, and correlating clip 108 may be implemented as follows. The identification placard 104, the arrangement clip 106, and correlating clip 108 push onto the IV tubes 102. For example, the identification placards 104 may be pushed onto the IV tubes 102 via the first tube capture portion 308. Similarly, the arrangement clips 106 may be pushed onto the IV tubes 102 via the second tube capture portion 408. Further, the correlating clips 108 may be pushed onto the IV tubes 102 similar to the first and second tube capture portions 308, 408.

Once the identification placards 104, the arrangement clips 106, and/or correlating clips 108 have been coupled to a plurality of respective IV tubes 102 such as depicted in FIG. 1, the medical practitioner may couple the identification placards 104 to one another and/or couple the arrangement clips 106 to one another. In this manner, the IV tubes 102 may be coupled together via the identification placards 104 and/or the arrangement clips 106.

In one example, the identification placards 104 and/or the arrangement clips 106 may be placed below a pump used to move fluids through the IV tubes to allow for labeling and grouping of the IV tubes 102. In one example, the arrangement clips 106 may be placed below the identification placards 104 to support the arrangement of the IV tubes 102 at a mid-line portion of the IV tubes 102. Further, the correlating clips 108 may be placed at or near the patient into whom the IV-deliverable composition is being administered in order to correlate the distinguishing characteristic of the correlating clips 108 to their respective identification placards 104 and/or the arrangement clips 106 as well as the IV tube to which they are respectively coupled. It is noted that the medical practitioner is to place identification placards 104, the arrangement clips 106, and/or the correlating clips 108 that include the same distinguishing characteristic onto the same IV tube 102 in order to ensure that the distinguishing characteristic identifies the same IV tube 102.

In the examples described herein, the first tube capture portion 308, the second tube capture portion 408, and/or the correlating clips 108 for connecting the components to the IV tubes 102 may be easier to push on than to pull off. This may assure that adjustments to the positions of the identification placards 104, the arrangement clips 106, and/or the correlating clips 108 are not easily made after once placed reducing any unintended changes to the system 100 without the medical practitioner considering his or her actions before making the change.

The male/female interlocking sections assist a user to organize and manage IV tubes 102 in clusters such as depicted by the IV tube organization apparatuses 110 described herein. Further, each of the IV tube organization apparatuses 110-1, 110-2, 110-s may be color coded to eliminate line tracing time and to avoid mistakes that may otherwise be made by a medical practitioner in distinguishing between the IV tubes 102. That elements of an IV tube apparatus and system 100 may all be one single color compared to the elements of another IV tube organization apparatus 110 of a different color.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. An intravenous (IV) tube organization system, comprising:
    a plurality of identification placards configured to individually couple to a corresponding plurality of IV tubes, the identification placards individually including:
        a first tube capture portion configured to couple the identification placards to a respective one of the IV tubes, and
        a data portion to receive and display information regarding the respective one of the IV tubes;

a plurality of arrangement clips configured to individually couple to a corresponding number of the IV tubes, the arrangement clips individually including:
  a second tube capture portion configured to couple the arrangement clips to the respective one of the IV tubes,
  a first fastener located on a first end of the arrangement clips, and
  a second fastener located on a second end of the arrangement clips, the first fastener to couplingly mate with the second fastener configured to couple a first arrangement clip of the plurality of arrangement clips to a second arrangement clip of the plurality of arrangement clips; and
a plurality of correlating clips, the correlating clips individually including:
  a third tube capture portion configured to couple the correlating clips to the respective one of the IV tubes,
wherein the identification placards, the arrangement clips, and the correlating clips have different structures relative to one another.

2. The system of claim 1, wherein the plurality of identification placards, the plurality of arrangement clips, and the plurality of correlating clips are grouped in a plurality of sets, a set including one of the plurality of identification placards, one of the plurality of arrangement clips, and one of the plurality of correlating clips, and
  wherein a first set varies from a second set by a distinguishing characteristic.

3. The system of claim 2, wherein the distinguishing characteristic includes at least one of a color, a texture, a pattern, or an image.

4. The system of claim 1, wherein the data portion includes:
  a medication entry area to indicate an IV-deliverable composition;
  a temporal entry area to indicate a time of an administration of the IV-deliverable composition; and
  an administrator identification entry area to indicate an administrator of IV-deliverable composition.

5. The system of claim 1, wherein the identification placards further include:
  a third fastener located on a first end of the identification placards; and
  a fourth fastener located on a second end of the identification placards, the third fastener configured to couplingly mate with the fourth fastener to couple a first identification placard of the plurality of identification placards to a second identification placard of the plurality of identification placards.

6. The system of claim 5, wherein:
  the second fastener and the fourth fastener include an anchor including a first portion and a second portion, the first portion being relatively wider than the second portion; and
  the first fastener and the third fastener include a snap-fit fastener configured to couple to the anchor,
  wherein the snap-fit fastener is elastically deformable to deflect around the first portion and configured to couple to the anchor at the second portion past the first portion.

7. The system of claim 1, wherein the first tube capture portion, the second tube capture portion, and the third tube capture portion include:
  a channel defined within the first tube capture portion, the second tube capture portion, and the third tube capture portion; and
  a first arm and a second arm defining an opening to the channel relatively narrower with respect to the channel.

8. An intravenous (IV) tube organization apparatus, comprising:
  a first identification placard configured to couple to a first IV tube of a plurality of IV tubes, the first identification placard including:
    a first tube capture portion configured to couple the first identification placard to the first IV tube, and
    a data portion to receive and display information regarding the first IV tube;
  a first arrangement clip configured to couple to the first IV tube; and
  a distinguishing characteristic associated with both the first identification placard and the first arrangement clip to differentiate the first identification placard and the first arrangement clip from a second identification placard and a second arrangement clip,
  wherein the first identification placard and the first arrangement clip have different structures relative to one another, and
  wherein the first arrangement clip includes:
    a second tube capture portion configured to couple the first arrangement clip to the first IV tube,
    a first fastener located on a first end of the first arrangement clip, and
    a second fastener located on a second end of the first arrangement clip, the first fastener configured to couplingly mate with the second fastener to couple the first arrangement clip to the second arrangement clip.

9. The apparatus of claim 8, wherein the first identification placard further includes:
  a third fastener located on a first end of the first identification placard; and
  a fourth fastener located on a second end of the first identification placard, the third fastener to mate with the fourth fastener.

10. The apparatus of claim 9, wherein:
  the second fastener and the fourth fastener include an anchor including a first portion and a second portion, the first portion being relatively wider than the second portion; and
  the first fastener and the third fastener include a snap-fit fastener configured to couple to the anchor,
  wherein the snap-fit fastener is elastically deformable to deflect around the first portion and couple to the anchor at the second portion past the first portion.

11. The apparatus of claim 8, further comprising at least one correlating clip, the at least one correlating clip including a third tube capture portion configured to couple the at least one correlating clip to the first IV tube.

12. The apparatus of claim 11, wherein the first tube capture portion, the second tube capture portion, and the third tube capture portion include:
  a channel defined within the first tube capture portion, the second tube capture portion, and the third tube capture portion; and
  a first arm and a second arm defining an opening to the channel relatively narrower with respect to the channel.

13. The apparatus of claim 8, wherein the distinguishing characteristic includes at least one of a color, a texture, a pattern, or an image.

14. The apparatus of claim 8, wherein the data portion includes:
  a medication entry to indicate an IV-deliverable composition;

a temporal entry to indicate a time of an administration of the IV-deliverable composition; and an administrator identification entry to indicate an administrator of IV-deliverable composition.

15. An intravenous (IV) tube organization system, comprising:

a plurality of IV tube apparatuses configured to couple to a corresponding number of IV tubes, the IV tube apparatuses individually comprising:

an identification placard configured to couple to one of the IV tubes, the identification placard including:

a first tube capture portion configured to couple the identification placard to a respective IV tube, and a data portion to receive and display information regarding the respective IV tube; and at least one correlating clip, the at least one correlating clip including:

a second tube capture portion configured to couple the at least one correlating clip to the respective IV tube, wherein the IV tube apparatuses include a distinguishing characteristic to differentiate the IV tube apparatuses from one another, wherein the identification placard and the at least one correlating clip have different structures relative to one another, and wherein the IV tube apparatuses further include:

an arrangement clip configured to couple to the respective IV tube, the arrangement clip including:

a third tube capture portion configured to couple the arrangement clip to the respective IV tube, a first fastener located on a first end of the arrangement clip, and a second fastener located on a second end of the arrangement clip, the first fastener configured to couplingly mate with the second fastener to couple the arrangement clip to another arrangement clip of another IV tube apparatus.

16. The system of claim 15, wherein the identification placard further includes:

a third fastener located on a first end of the identification placard; and a fourth fastener located on a second end of the identification placard, the third fastener configured to couplingly mate with the fourth fastener to couple the arrangement clip to another arrangement clip of another IV tube apparatus, wherein:

the second fastener and the fourth fastener include an anchor including a first portion and a second portion, the first portion being relatively wider than the second portion; and the first fastener and the third fastener include a snap-fit fastener configured to couple to the anchor, wherein the snap-fit fastener is elastically deformable to deflect around the first portion and couple to the anchor at the second portion past the first portion.

17. The system of claim 15, wherein the first tube capture portion, the second tube capture portion, and the third tube capture portion include:

a channel defined within the first tube capture portion, the second tube capture portion, and the third tube capture portion; and a first arm and a second arm defining an opening to the channel relatively narrower with respect to the channel.

18. The system of claim 15, wherein the distinguishing characteristic includes at least one of a color, a texture, a pattern, or an image.

* * * * *